United States Patent [19]

Froning et al.

[11] Patent Number: 4,511,356

[45] Date of Patent: Apr. 16, 1985

[54] CANNULA, OBTURATOR, STYLET AND NEEDLE HUB CONNECTORS FOR LUMBAR DISC PUNCTURE

[75] Inventors: Edward C. Froning, P.O. Box 1768, Rancho Santa Fe, Calif. 92067; Gregory S. Graham, Ventura, Calif.

[73] Assignee: Edward C. Froning, Rancho Santo Fe, Calif.

[21] Appl. No.: 468,379

[22] Filed: Feb. 22, 1983

[51] Int. Cl.³ .................... A61M 5/00; A61M 5/04
[52] U.S. Cl. .................... 604/164; 604/198
[58] Field of Search ............ 604/158, 161, 164, 165, 604/44, 196, 198, 272

[56] References Cited

U.S. PATENT DOCUMENTS

| | | | |
|---|---|---|---|
| 2,923,295 | 2/1960 | Guerriero | 604/164 |
| 3,454,006 | 7/1969 | Langdon | 604/164 |
| 3,896,810 | 7/1975 | Akiyama | 604/272 |
| 3,906,946 | 9/1975 | Nordström | 604/164 |
| 4,013,080 | 3/1977 | Froning | 604/165 |
| 4,137,916 | 2/1979 | Killman et al. | 604/170 |
| 4,292,970 | 10/1981 | Hession, Jr. | 604/164 |
| 4,317,445 | 3/1982 | Robinson | 604/168 |
| 4,326,519 | 4/1982 | D'Alo et al. | 604/165 |
| 4,417,886 | 11/1983 | Frankhouser et al. | 604/170 |

Primary Examiner—C. Fred Rosenbaum
Assistant Examiner—C. W. Shedd
Attorney, Agent, or Firm—Julian Caplan

[57] ABSTRACT

A cannula has a hub formed with a hollow upward projection on its top which communicates with a lumen having a bore in the hub and the cannula itself. On one side of the hub is a vane having converging sides and a rounded end. The vane has a horizontal opening extending inward and the portion above the opening is cut away so that it is about half the thickness of the portion below the opening. A stylet or an obturator fits through the hollow projection, bore and cannula, extending to the tip of the cannula. A hub on the stylet or obturator has a socket to receive the cannula hub projection and a vane formed with a cutout to receive the portion above the opening of the cannula hub, the portion of the stylet or obturator vane below the cutout locking in the opening in the cannula hub. A hollow needle also fits through the hollow projection, bore and cannula and has a hub formed with a socket to receive the hollow projection and a fitting for attachment to a syringe. The end of the needle is bevelled and frequently curved. A vane on the needle hub orients the end of the needle by the alignment of the needle vane with the bevel.

11 Claims, 6 Drawing Figures

CANNULA, OBTURATOR, STYLET AND NEEDLE HUB CONNECTORS FOR LUMBAR DISC PUNCTURE

This invention relates to a new and improved cannula, obturator, stylet and needle hub connector for use in operations such as lumbar disc puncture for chemonucleolysis. Thus diagnostic radiographic contrast fluids are injected in the nucleous pulposus and later fluids containing the enzyme chymopapain are injected to decompress the disc. This invention is an improvement upon U.S. Pat. No. 4,013,080.

Thus, in accordance with the present invention, instruments such as stylets and obturators and disc penetrating needles are inserted in a cannula which functions as a guide for the other instruments. The advantages of such instruments are set forth in said U.S. Pat. No. 4,013,080 and many of these advantages apply equally to the present invention.

The improvement of the present invention resides in improved hubs on the cannula and the other instruments which insure that the instruments are properly located longitudinally of the cannula. Further, when a curved needle is used for disc injection, the hubs serve as guides for visible confirmation of the proper position of the needle. The vane on the needle hub is aligned with the bevel on the distal of the needle, to provide the surgeon constant awareness of the orientation of the curvature of the needle, even when the bevel is out of sight.

Another advantage of the shape of the hubs hereinafter described is that they are convenient to assist the surgeon in turning the instruments relative to each other and relative to the injection syringe.

It is desirable that the obturator and stylet lock in the cannula and the hubs of the instrument are shaped to facilitate locking and, when necessary, unlocking.

Other objects of the present invention will become apparent upon reading the following specifications and referring to the accompanying drawings in which similar characters of reference represent corresponding parts in each of several views.

Figure 3:
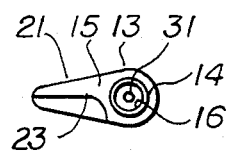
FIG. 3 is a section taken substantially along the line 3—3 of FIG. 1.

Cannula 11 is a thin walled tube or lumen having an inside diameter which receives the other instruments hereinafter described. The distal end 12 of cannula 11 is rounded in one case and tapered in another. The distal of cannula tubing may be shaped squared off, tapered, or other configuration according to the function required. Hub 13 is fixed to the proximal end of cannula 11 and has a flat top surface 15 from which projects round external hollow upward projection 14. The interior of the projection 14 is a downwardly-inwardly tapered bore 16 which merges into a cylindrical bore 17 in the hub 13, having a reduced diameter seat 18 for the upper end of the cannula 11. Solder or other means may secure the cannula in place. The tapered bore 16 assists in the insertion of the instruments which fit through the cannula. Hub 13 has a lateral vane 21 having sides which converge at about a 12° angle and a rounded outward extremity. Vane 21 is cut into two sections by a horizontal opening 22. The top portion 24 of the vane 21 above the opening 22 has a curved cutaway 23, best shown in FIG. 3.

Figure 1:
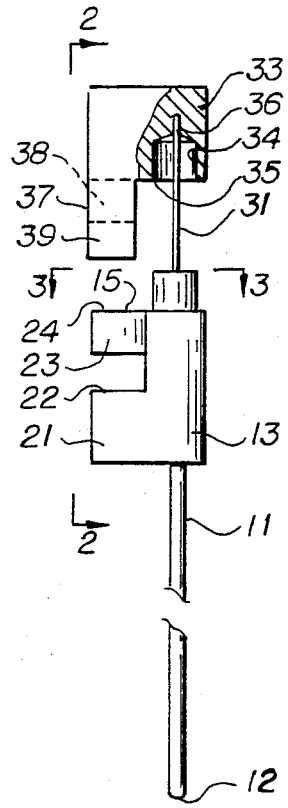
FIG. 1 is a view showing the obturator and cannula hubs prior to locking.
Figure 1A:
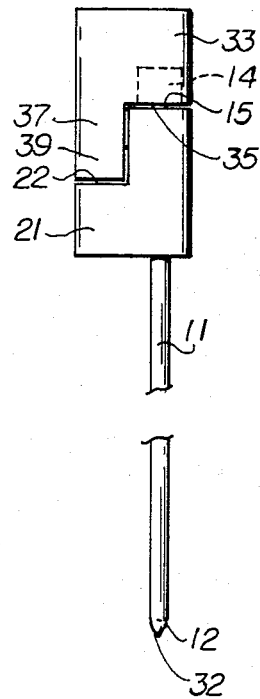
FIG. 1A is a view similar to FIG. 1 showing the hubs locked.

Stylet 31 has a sharp distal point 32 which extends slightly beyond the rounded distal end 12 of the cannula 11. It is important that the point 32 extend slightly beyond the end 12 and the construction of the mating hub 33 with hub 13 as hereinafter explained, accomplishes this result. Similarly, although not shown in the accompanying drawings, but as is explained in U.S. Pat. No. 4,013,080, an obtuator (not shown) may also be inserted and locked in position in the cannula 11 and has its rounded point positioned approximately in the same position as the point 32 of the stylet 31 shown in FIG. 1A. The hub 33 of stylet 31 has a flat bottom surface 35 into which is recessed socket 34 shaped to receive the projection 14 of hub 13. The upper end of the stylet 31 is secured in seat 36 immediately above socket 34 so that the stylet 31 is centrally disposed relative to the socket 34. The sides of hub 33 converge at the same angles as the sides of the hub 13 and the outer end is rounded. At the left end of hub 13 as viewed in FIGS. 1 and 1A, there is a downward projection 37 formed with projection 37 formed with a lateral cutout 38 on one side which has dimensions enabling it to receive the top portion 24 of hub 21 above cutout 22 as the latter has been trimmed away in the cutout portion 23. Below cutout 38 is a locking portion 39 which is dimensioned to fit into the opening 22.

To attach the stylet 31 within the cannula 11, the point 32 is inserted into the bore 16 in the projection 14 and the hub 33 pushed toward the hub 13. The two hubs are rotated slightly out of alignment so that the locking portion 39 can clear the upper portion 24 of the vane 21. Surface 35 is pushed into contact with surface 15. Thereupon, the hub 33 is twisted so that the locking portion 39 enters the opening 22. This holds the hubs 13 and 33 together. It also insures that the point 32 is properly located projecting beyond the lower end 12 of the cannula 11. To disengage the stylet 31, the hub 33 is rotated counterclockwise as viewed in FIG. 3 so that the locking portion 39 clears the opening 22, whereupon the hub 33 is pulled upward relative to the hub 13.

It will be understood that the insertion and locking of the obturator (not shown) is similarly accomplished.

Figure 4:
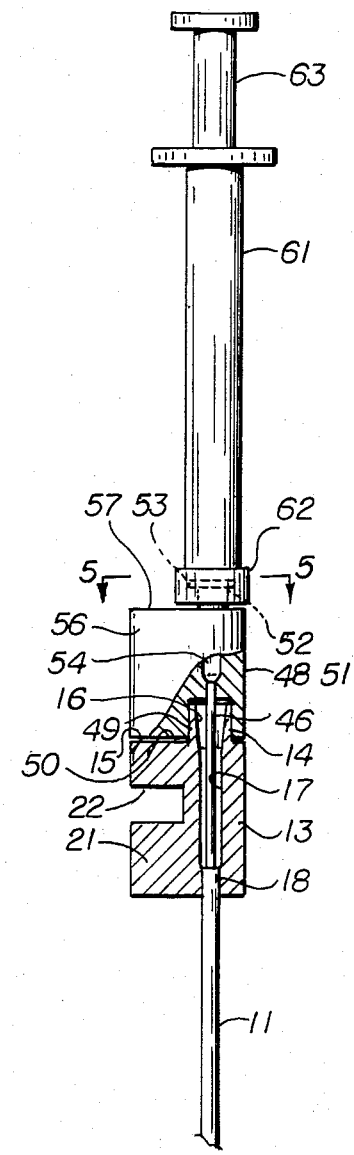
FIG. 4 is a view similar to FIG. 1A showing a needle and syringe attached to a cannula.
Figure 2:
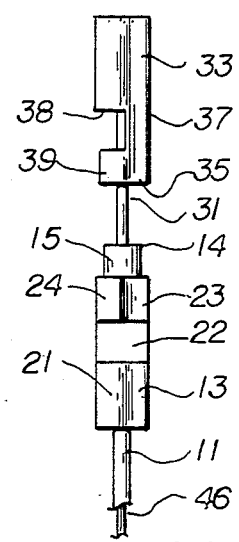
FIG. 2 is a side elevation from the left of FIG. 1.
Figure 5:
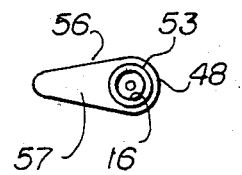
FIG. 5 is a sectional view taken substantially along the line 5—5 of FIG. 4 with the syringe removed.

Directing attention now to FIGS. 4 and 5, after the cannula 11 has been brought into proximity to a lumbar disc in the manner explained in U.S. Pat. No. 4,013,080, the obturator is removed and a hollow needle 46 having a beveled tapered point 47 is inserted. It is desirable, and in many cases necessary, that the needle 46 be bent in a curve as shown in the lower part of FIG. 4 for the purpose and by the means explained in said U.S. Pat. No. 4,013,080. It is also very important that the surgeon at all times be aware of the direction in which the bevelled point 47 is directed. For this purpose, hub 48 is installed on the upper end of the needle 46, said hub having a flat bottom 50 into which is recessed socket 49 shaped to receive the projection 14. Above socket 49 is a seat 51 for the upper end of needle 46 which may be soldered or otherwise held held in place. The upper surface of hub 48 is flat with an upward projection 52 having a luer fitting 53 which is hollow and communicates with bore 54 in hub 48 and thence with needle 46 so that fluid discharged from syringe barrel 61 is delivered to the point 47. The lower end of barrel 61 has a collar 62 with an internal luer fitting mating with the fitting 53. Any conventional plunger 63 may be used in the barrel 61.

As best shown in FIGS. 4 and 5, hub 48 has a vane 56 projecting to one side and in alignment with the taper of the point 47. Vane 56 has sides which converge at the same angle as the sides of vane 21 and, similarly, has a rounded lock 39 end. It is not desireable that there be any locking means on hub 56 similar to the lock 39 of the hub 33 of the stylet 31, or obturator.

What is claimed is:

1. A canula for use with an instrument having a shaft, an instrument hub on said instrument having a socket in its bottom surface and an instrument vane extending laterally relative to said shaft, said instrument vane having first and second instrument vane sides, said instrument vane having a downward projection, said instrument vane being formed with a cut-away portion and having a lock wider than said cut-away portion below said cut-away portion comprising a lumen, said lumen being shaped to receive said shaft, a cannula hub on the proximal end of said lumen having a bore aligned with said lumen, a flat top, a hollow projection extending up from said top aligned with said bore shaped to fit into said socket and a cannula vane extending laterally relative to said lumen, said cannula vane having first and second cannula vane sides, said cannula vane being formed with a notch extending inward from the outer end of said cannula vane dividing said cannula vane into upper and lower portions, said notch being shaped to receive said lock, said upper portion being cut away on said first cannula vane side to about the vertical midsection of said cannula vane to fit against said cut-away portion of said instrument vane, said first and second cannula vane sides being parallel to said first and second instrument vane sides in the assembled position of said instrument and said cannula.

2. A cannula according to claim 1 in which said first and second sides cannula vane converge outwardly.

3. A cannula according to claim 1 in which said bore diverges upwardly.

4. In combination, a cannula according to claim 1 and an instrument having a shaft fitting inside said lumen of a length to protrude slightly beyond the distal of said lumen, an instrument hub on said instrument having a socket in its flat bottom surface shaped to receive said hollow projection and an instrument vane extending laterally relative to said shaft, said instrument vane having first and second instrument vane sides parallel to the first and second cannula vane sides when said combination is assembled, said second vane having a downward projection, the second instrument vane side of the upper portion of said instrument vane being cut away complementary to the shape of the upper portion of said cannula vane, the lower portion of said instrument vane below the upper portion thereof being complementary to said notch in said cannula vane.

5. The combination of claim 4 in which the first and second cannula vane sides converge outwardly and said first and second instrument vane sides converge outwardly and are co-planar with the first and second cannula vane sides in the assembled position of said combination.

6. The combination of claim 4 in which said instrument is a stylet having a sharp point.

7. The combination of claim 4 in which said instrument is an obturator.

8. In combination, a cannula according to claim 1 and a hollow needle fitting inside said lumen of a length to extend beyond the distal of said lumen, a needle hub having a flat bottom surface formed with a socket to receive said projection and an upward projection on its top shaped to fit with a syringe, said needle hub having a needle vane extending laterally relative to said needle.

9. The combination of claim 8 in which the distal of said needle is formed with a bevel and said needle vane is aligned with said bevel.

10. The combination of claim 9 in which said needle is curved in alignment with said needle vane.

11. The combination of claim 10 in which said first and second canula vane sides converge outwardly and in which said needle vane has first and second needle vane sides converging outwardly and being co-planar with said first and second cannula vane sides to indicate the position of the curvature of said needle.

* * * * *